(12) United States Patent
Kim et al.

(10) Patent No.: US 9,709,495 B2
(45) Date of Patent: Jul. 18, 2017

(54) SYSTEM FOR EVALUATING DISPLAYING QUALITY OF TRANSPARENT DISPLAY AND METHOD THEREOF

(71) Applicant: LG DISPLAY CO., LTD., Seoul (KR)

(72) Inventors: Jaehong Kim, Paju-si (KR); Dongyou Lee, Seoul (KR); Moojong Lim, Seoul (KR); Kyongho Lim, Paju-si (KR); Hongseop Shin, Paju-si (KR); Sunhee Park, Seoul (KR)

(73) Assignee: LG DISPLAY CO., LTD., Seoul (KR)

( * ) Notice: Subject to any disclaimer, the term of this patent is extended or adjusted under 35 U.S.C. 154(b) by 449 days.

(21) Appl. No.: 14/586,496

(22) Filed: Dec. 30, 2014

(65) Prior Publication Data
US 2015/0308951 A1 Oct. 29, 2015

(30) Foreign Application Priority Data
Apr. 29, 2014 (KR) ........................ 10-2014-0051467

(51) Int. Cl.
G01N 21/00 (2006.01)
G01N 21/59 (2006.01)
G01N 21/95 (2006.01)

(52) U.S. Cl.
CPC ............ *G01N 21/59* (2013.01); *G01N 21/95* (2013.01); *G01N 2021/9513* (2013.01)

(58) Field of Classification Search
CPC ................ G01N 21/59; G01N 21/255; G01N 2021/8832; G01N 2021/9513
USPC ........................... 356/239.1, 239.2; 349/192
See application file for complete search history.

(56) References Cited

U.S. PATENT DOCUMENTS

| | | | |
|---|---|---|---|
| 7,483,550 B2 * | 1/2009 | Oka .................. | G09G 3/006 348/180 |
| 9,341,572 B2 * | 5/2016 | Ma .................. | G01N 21/534 |
| 2006/0023144 A1 | 2/2006 | Sakamoto | |

FOREIGN PATENT DOCUMENTS

| | | |
|---|---|---|
| CN | 1912708 A | 2/2007 |
| CN | 102967443 A | 3/2013 |
| CN | 103576357 A | 2/2014 |

\* cited by examiner

*Primary Examiner* — Hoa Pham
(74) *Attorney, Agent, or Firm* — Birch, Stewart, Kolasch & Birch, LLP

(57) ABSTRACT

A system for evaluating a quality of a transparent display, the system including: a background including any one of a full white pattern, a full black pattern, and a circle white pattern; a light detector positioned a first distance away from the background to measure luminance of the full white pattern, the full black pattern and the circle white pattern; and a circle transparent pattern displayed on the transparent display by passing light from at least one of the full white pattern, the full black pattern and the circle white pattern, further the transparent display is positioned between the background and the light detector and at a second distance away from the light detector, further a purity of the transparent display is calculated based on luminance of the full white pattern, the full black pattern, and the circle white pattern as measured by the light detector through the transparent display.

16 Claims, 9 Drawing Sheets

SYSTEM FOR EVALUATING DISPLAYING QUALITY OF TRANSPARENT DISPLAY AND METHOD THEREOF

This application claims the benefit of Korea Patent Application No. 10-2014-0051467 filed in the Republic of Korea on Apr. 29, 2014, which is incorporated herein by reference for all purposes as if fully set forth herein.

BACKGROUND OF THE INVENTION

Field of the Invention

The present invention relates to a system for evaluating the display quality of a transparent display and method thereof. Particularly, the present invention provides a new standard (or, index, measure, scale) and a system for evaluating how well a transparent display presents display information with the background view (e.g., the scene behind the display/objects viewed through the display) through the display at the same time.

Discussion of the Related Art

Various flat panel display devices providing video information including still pictures, moving pictures and/or animations are developed for overcoming many drawbacks of the cathode ray tube such as its heavy weight and bulk volume. Flat panel display devices include the liquid crystal display device (LCD), the field emission display (FED), the plasma display panel (PDP) and the electroluminance device (EL).

The liquid crystal display and the organic light emitting diode display are representative of flat displays that are widely applied in various appliances including portable devices and/or television sets. However, these flat panel displays are developed just for a display system, but they are not applied to various applications. For example, a transparent display displays video information on its screen when the display is activated and the user can see objects behind the display through the display panel when it is not activated. However, the standard for evaluating the quality of a transparent display is not clear and it is very hard for a user and/or consumer to decide which display is suitable for his or her displaying environment and/or purpose.

In more detail, the transparent display is like see through glass when it is not operated, and presents video information when it is operated. In some instances, when it is activated, the user sees only the video information presented by the transparent display. In other instances, even when the transparent display is operated, the user may see the video information and the background scene behind the display panel through the display panel (e.g., a view of the objects behind the display). For example, a heads up display (HUD) is a typical example of such a transparent display. Until now, such a transparent display is only used in environments in which a very expensive display system is applied without regard to the price in the market. However, the requirement of a transparent display in various fields including advertising displays and home appliances is increasing.

FIG. 1 is a perspective diagram illustrating the structure of a transparent display using a liquid crystal display. The transparent liquid crystal display includes a liquid crystal display panel LCDP, a light guide LG and a light source. The liquid crystal display panel LCDP includes two polarization sheets and a liquid crystal panel LCP inserted between the two polarization sheets. The liquid crystal panel LCP includes an upper substrate SU, a lower substrate SL and a liquid crystal layer LC inserted between the two substrates SU and SL.

At the upper side and the lower side of the liquid crystal panel LCP, an upper polarization sheet PU and a lower polarization sheet PL are disposed, respectively. On the inner surfaces of the upper substrate SU and the lower substrate SL, a plurality of lines and black matrixes are disposed as defining a plurality of pixel areas arranged in a matrix manner, and the common electrode and the pixel electrode for driving the liquid crystal layer LC. Further, a color filter for representing a full color picture is included. The upper polarization sheet PU is disposed on the outer surface of the upper substrate SU, and the lower polarization sheet PL is disposed on the outer surface of the lower substrate SL.

Generally, the light axis of the upper polarization sheet PU is perpendicular to the light axis of the lower polarization sheet PL so that a real black level can be reproduced exactly. However, for a transparent display, if the upper polarization sheet PU and the lower polarization sheet PL are disposed like they are in a common liquid crystal display, when it is not activated, light cannot pass through the liquid crystal display panel LCDP. The situation in which the light axis of the upper polarization sheet PU is perpendicular to that of the lower polarization sheet PL is referred to as the 'Normally Black (or NB) mode,' because it represents the black level under normal conditions (e.g., while not operating).

For a transparent display, the display can be in a transparent state when the liquid crystal display panel LCDP is not activated. Therefore, it is preferable that the liquid crystal display panel LCDP for the transparent display be made in the 'Normally White (or NW) mode' which represents the white level under normal conditions. Unlike the normally black mode, the normally white mode cannot be acquired by the parallel arrangement of the light axes of the upper polarization sheet PU and the lower polarization sheet PL. The polarization characteristics of the liquid crystal layer LC used for the liquid crystal panel LCP should be considered.

For the vertical electric field type of liquid crystal display using a twisted nematic mode liquid crystal layer, even though the light axes of the upper polarization sheet PU and the lower polarization sheet PL are perpendicular, the normally white mode can be acquired. On the contrary, for the horizontal electric field type of liquid crystal display, the normally white mode can be established with the light axes of the upper polarization sheet PU and the lower polarization sheet PL being perpendicular.

Under the liquid crystal display panel LCDP, the light guide LG and the light source LS are disposed. The light source LS is disposed at one side surface of the light guide LG to provide light to the light guide LG. The light guide LG diffuses light from the light source LS throughout the whole inner space of the light guide LG, and refracts light to the upper surface facing the liquid crystal display panel LCDP. To do this, a reflective pattern is disposed on the rear surface (or, bottom surface) of the light guide LG. Since the light guide LG should ensure a transparent condition, the reflective pattern would be one of the prism pattern, the lenticular lens pattern or the micro lens pattern.

As mentioned above, when the transparent display is not activated, it is in a transparent condition like clear glass. On the contrary, when electric power is supplied for using it as a display device, it can provide video information together with the scene behind the display (e.g., objects behind the display remain viewable). Further, the transparent display should include a back light unit that ensures the transparent property, in contrast to a normal liquid crystal display. Therefore, the optical sheets used in normal liquid crystal displays for enhancing the brightness of the back light should not be used for a transparent display.

Hereinafter, referring to FIGS. 2 and 3, a related art transparent display using the organic light emitting diode display will be explained. In particular, FIG. 2 is a plane view illustrating the structure of a transparent organic light emitting diode display, and FIG. 3 is a cross sectional view illustrating the structure of the bottom emission type of transparent organic light emitting diode display along the cutting line I-I' of FIG. 2. The bottom emission type of transparent organic light emitting diode display according to the related art includes a switching thin film transistor ST, a driving thin film transistor DT connected to the switching thin film transistor ST, and an organic light emitting diode OLE connected to the driving thin film transistor DT.

One pixel area of the transparent organic light emitting diode display includes a light emitting area LEA for representing the video information and a transparent area TRA for penetrating or transmitting/communicating the background scene. For example, the pixel area is defined by a scan line SL, a data line DL and a driving current line VDD, and the pixel area is divided into the light emitting area LEA and the transparent area TRA. Further, the pixel area includes a non-light emitting area where any light for representing video information and from the background scene are not suggested.

The switching thin film transistor ST is formed where the scan line SL and the data line DL cross each other. The switching thin film transistor ST acts for selecting the pixel connected to the switching thin film transistor ST. The switching thin film transistor ST includes a gate electrode SG branching from the scan line SL, a semiconductor channel layer SA overlapping with the gate electrode SG, a source electrode SS and a drain electrode SD. The driving thin film transistor DT drives an anode electrode ANO of the organic light emitting diode OLE disposed at the pixel selected by the switching thin film transistor ST. The driving thin film transistor DT includes a gate electrode DG connected to the drain electrode SD of the switching thin film transistor ST, a semiconductor channel layer DA, a source electrode DS connected to the driving current line VDD, and a drain electrode DD.

The drain electrode DD of the driving thin film transistor DT is connected to the anode electrode ANO of the organic light emitting diode OLE. The organic light emitting layer OL is inserted between the anode electrode ANO and the cathode electrode CAT. Further, the cathode electrode CAT is connected to the base voltage (or, ground voltage) VSS. A storage capacitance Cst is disposed between the gate electrode DG of the driving thin film transistor DT and the driving current line VDD or between the gate electrode DG of the driving thin film transistor DT and the drain electrode DD of the driving thin film transistor DT.

In the view of the cross sectional structure shown in FIG. 3, the gate electrodes SG and DG of the switching thin film transistor ST and the driving thin film transistor DT are formed on the substrate SUB of the transparent organic light emitting diode display. On the gate electrodes SG and DG, the gate insulator GI is deposited. On the gate insulator GI overlapping with the gate electrodes SG and DG, the semiconductor layers SA and DA are formed, respectively. Further, on the semiconductor layer SA and DA, the source electrode SS and DS and the drain electrode SD and DD facing and separated from each other are formed. The drain electrode SD of the switching thin film transistor ST is connected to the gate electrode DG of the driving thin film transistor DT via the drain contact hole DH penetrating the gate insulator GI. In addition, the passivation layer PAS is deposited on the substrate SUB having the switching thin film transistor ST and the driving thin film transistor DT.

In some instances, a color filter CF is further disposed on the passivation layer PAS. In these instances, it is preferable that the color filter CF be formed within the light emitting area LEA. For example, the color filter CF can be formed where the anode electrode ANO would be formed later. For representing full color, the color filter CF may include any one of a red pigment, a green pigment and a blue pigment. The color filter CF set including the red color filter R, the green color filter G and the blue color filter B is arrayed in a matrix manner.

As mentioned above, the substrate SUB having the thin film transistors ST and DT has an uneven surface and level differences because there are many elements. It is preferable for the organic light emitting layer OL to be formed on an even surface to ensure uniform light emission distribution over all of the area of the organic light emitting layer OL. Therefore, in order to make the surface of the substrate SUB smooth, the over coat layer OC (or, the planar layer) is deposited over the substrate SUB.

On the over coat layer OC, an anode electrode ANO of the organic light emitting diode OLE is formed. Here, the anode electrode ANO is connected to the drain electrode DD of the driving thin film transistor DT via the contact hole formed at the over coat layer OC and the passivation layer PAS. It is preferable that the anode electrode ANO is formed within the light emitting area LEA. The ratio of the light emitting area LEA and the transparent area TRA is not strictly defined. That is, it can be selected among the various ratio values according to the specification for the brightness of the display and purpose of the display.

In the bottom emission type of organic light emitting diode display representing full color, the anode electrode includes a transparent conductive material such as an indium tin oxide (or, ITO) or an indium zinc oxide (or, IZO). A bank BN is formed on the substrate SUB having the anode electrode ANO. It is preferable that the bank BN separates the light emitting area LEA and the transparent area TRA and has apertures exposing each area, respectively. If required, the bank BN can have one aperture exposing the light emitting area LEA and the transparent area TRA. Otherwise, the bank BN has a pattern for exposing the light emitting area LEA but not exposing the transparent area TRA. The exposed portion of the anode electrode ANO by the bank BN would be the actual light emitting area.

On the surface of the substrate SUB where the anode electrode ANO of the light emitting area LEA is exposed from the bank BN, the organic light emitting layer OL is formed. For the bottom emission type in which the color filter CF is disposed under the anode electrode ANO, the organic light emitting layer OL may include an organic material which can generate white color. On the organic light emitting layer OL, the cathode electrode CAT is formed. Consequently, the organic light emitting diode OLE including the anode electrode ANO, the organic light emitting layer OL and the cathode electrode CAT and driven by the driving thin film transistor DT is formed.

A transparent display having the structure mentioned above appears as transparent glass when it is not activated so that the background scene can be seen by a user located in front of the display. When the user turns on the display, the user can see the video information with the background scene or without the background scene. This can be applied to various applications.

The transparent display should have a good property for displaying high quality video information and for providing high visual quality of the background scene passing through the display panel. However, the standard (or, index, measure, scale or barometer) for evaluating the visual quality and/or property of a transparent display is not clearly defined in the field market. Until now, the quality of a transparent display has been evaluated by adopting the measurement standards for transparent substrates such as bare glass. For example, the standard for evaluating a transparent substrate according to the related art is measurement of the haze or the clarity.

The haze means the diffusing degrees of the light is defined by the percent of transmitted light that is scattered so that its direction deviates more than a specified angle from the direction of the incident beam (ASTM D 1003). In this test method, the specified angle is 2.5° (0.044 rad). FIG. 4 is a schematic diagram illustrating the method for measuring the haze according to the related art. The light IL radiated from the light source LS enters into the measuring instrument HMD via the entrance ETR after passing through the transparent display TS. Here, the light TL passing through the transparent display TS is scattered. The haze measuring instrument HMD can measure the light out of the exit EXT, where the measured light is within the specified angle)(2.5° about the light incident axis. Using the instrument as shown in FIG. 4, the total amount of the light, $T_t$, passing through the transparent display TS and measured at the entrance ETR and the partial amount of the light, $T_d$, propagating within the specified angle)(2.5° at the exit EXT are measured, respectively. And then, the haze is calculated by the following Equation 1.

$$\text{Haze} = \frac{T_d}{T_t} \times 100(\%) \quad \text{(Equation 1)}$$

The clarity is defined as the ability to transmit image-forming light, in correlation with its regular transmittance (ASTM D 1746-03), and can be acquired as measuring the ratio of the amount of light passing within the specific angle 2.5° to the whole amount of light transmitted through the ring pattern with the contrast modulation. FIG. 5 is a schematic diagram illustrating the related art method for measuring the clarity. The light IL is radiated from the light source LS. The radiated light TL is measured using the clarity measuring instrument CMD. Disposing a ring pattern CP at the exit EXT of the clarity measuring instrument CMD, and measuring the amount of the light, the clarity can be calculated. As shown in FIG. 5, the light amount, $I_R$, passing through the ring pattern RS and the light amount, $I_c$, passing through the center circle pattern CS are measured and then the clarity is calculated by the following Equation 2.

$$\text{Clarity} = \frac{I_C - I_R}{I_C + I_R} \times 100(\%) \quad \text{(Equation 2)}$$

However, these values cannot accurately evaluate the quality of a transparent display exactly. For example, a transparent display having a high value of the haze or the clarity has a worse quality than a transparent display having a lower value of the haze or the clarity.

As mentioned above, at least on one surface of the transparent display (for ensuring the transparent property), various elements configuring the pixel are formed, even though they are not easily seen. Therefore, when light from the background scene passes through the transparent display panel, the light has various optical effects due to the different elements. For example, the incident light from the rear surface of the transparent display may be refracted, reflected and/or absorbed as the light passes through the transparent display panel. Further, because the various elements have tiny patterns, these patterns act as slits so that various optical phenomena such as diffraction and/or scattering occur.

Unlike a transparent liquid crystal display, a transparent organic light emitting diode display has no transparent electrode in the transparent area TRA so that the background light may not be diffracted and/or refracted by the elements. As a result, it has a better transparent quality than a liquid crystal display. However, there are lines disposed between the transparent areas TRA. Especially, for a high resolution transparent organic light emitting diode display, the background light may be easily diffracted and/or refracted by the display elements so that the transparent quality is degraded.

The haze and the clarity are the evaluation standards for bare glass. Therefore, they are not suitable for evaluating the transparent property of a transparent display panel in which various transparent elements are disposed thereon. Consequently, any related standard cannot evaluate the quality of a transparent display exactly or correctly, and there is no method for evaluating the transparent display quality.

SUMMARY OF THE INVENTION

In order to overcome the above mentioned drawbacks, one object purpose of the present invention is to provide a system for evaluating the quality of a transparent display and a method for measuring the quality of a transparent display.

Another object of the present invention is to provide a novel standard in which the measured property is proportional to the actual quality of a transparent display evaluated by the user.

Still another object of the present invention is to provide a system for measuring the new standard for evaluating the quality of a transparent display, and a method for measuring the same.

In order to accomplish the above objects, embodiments of the present invention provide a system for evaluating a quality of a transparent display including: a background representing any one of a full white pattern, a full black pattern, and a circle white pattern; a light detector disposed with a first distance apart from the background for measuring luminance of the full white pattern, the full black pattern and the circle white pattern; and a circle transparent pattern displayed on the transparent display passing lights from at least one of the full white pattern, the full black pattern and the circle white patter, wherein the transparent display is placed between the background and the light detector and at a position with a second distance apart from the light detector, wherein a purity of the transparent display is calculated by the following equation 1 with a full white luminance of the full white pattern, a full black luminance of the full black pattern and a circle white luminance of the circle white pattern which are measured by the light detector through the transparent display.

$$\text{Purity}(\%) = \frac{L_{CW} - L_{FK}}{L_{FW} - L_{FK}} \times 100 \quad \text{(Equation 1)}$$

Here, $L_{FW}$ is the full white luminance, $L_{FK}$ is the full black luminance, and $L_{CW}$ is the circle white luminance.

In one embodiment, the first distance is 1.5 m and the second distance is 0.5 m.

In one embodiment, the circle white pattern includes a circle pattern having a first diameter and a full white level, and an ambient surrounding the circle pattern and having a full black level, and wherein the first diameter corresponds to a 0.2° height based on a point 1.5 m apart.

In one embodiment, the circle transparent pattern includes a circle pattern having a maximum white level of the transparent display and an ambient surrounding the circle pattern having a maximum black level of the transparent display, and wherein the second diameter is selected as one condition in which the second diameter corresponds to a 0.2° height based on a point 1.5 m apart, and that the second diameter covers an area including at least 500 pixels of the transparent display.

In one embodiment, the circle white pattern has a shape and a size the same as a receiving lens of the light detector, and a center of the circle white pattern, a center of the circle transparent pattern, and a center of the receiving lens are aligned onto a straight line.

In one embodiment, the background further represents a circle black pattern, the light detector further measures a luminance of the circle black pattern passing through the circle transparent pattern displayed on the transparent display, wherein a criteria of the purity is calculated by the following equation with the circle black luminance of the circle black pattern is measured by the light detector.

$$\text{Criteria} = \frac{||L_{FW} - L_{CW}| - |L_{FK} - L_{CK}||}{|L_{FW} - L_{CW}|} \times 100 \leq 2(\%)$$

Here, $L_{FW}$ is the full white luminance, $L_{FK}$ is the full black luminance, $L_{CW}$ is the circle white luminance, and $L_{CK}$ is the circle black luminance.

In one embodiment, the circle black pattern includes a circle pattern of full black level having a first diameter and an ambient of full white level, and the first diameter is corresponding to a 0.2° height based on a point 1.5 m apart.

In one embodiment, the light detector further measures a reference full white luminance of the full white pattern, a reference full black luminance of the full black pattern and a reference circle white luminance of the circle white pattern, without the transparent display, a reference purity is calculated by the following equation 2, $$P_{ref} = \frac{L_{CW,w/o} - L_{FK,w/o}}{L_{FW,w/o} - L_{FK,w/o}} \quad \text{(Equation 2)}$$

here, $L_{FW,w/o}$ is the reference full white luminance, $L_{FK,w/o}$ is the reference full black luminance, and $L_{CW,w/o}$ is the reference circle white luminance.

The purity calculated by equation 1 is decided as a measured purity, and a new purity of the transparent display is calculated by the following equation 3 with the reference purity and the measured purity.

$$\text{Purity}(\%) = \frac{P_{exp}}{P_{ref}} \times 100 \quad \text{(Equation 3)}$$

Here, $P_{exp}$ is the measured purity, and $P_{ref}$ is the reference purity.

Further, the present invention can provide a method for evaluating a quality of a transparent display comprising: displacing a background configured to represent any one of a full white pattern, a full black pattern, and a circle white pattern and a light detector with a first distance apart from the background, and aligning a center of the circle white pattern and a center of a receiving lens of the light detector onto an alignment axis; placing the transparent display between the background and the light detector and at a position with a second distance apart from the light detector; displaying a circle transparent pattern on a center of the transparent display, and aligning a center of the circle transparent pattern onto the alignment axis; measuring luminance of the full white pattern, the full black pattern and the circle white pattern represented on the background, through the transparent display; and calculating a purity of the transparent display based on a full white luminance of the full white pattern, a full black luminance of the full black pattern and a circle white luminance of the circle white pattern, wherein the purity is calculated by the following equation 1.

$$\text{Purity}(\%) = \frac{L_{CW} - L_{FK}}{L_{FW} - L_{FK}} \times 100 \quad \text{(Equation 1)}$$

Here, $L_{FW}$ is the full white luminance, $L_{FK}$ is the full black luminance, and $L_{CW}$ is the circle white luminance.

In one embodiment, the first distance is 1.5 m and the second distance is 0.5 m.

In one embodiment, the circle white pattern includes a circle pattern having a first diameter and a full white level, and an ambient surrounding the circle pattern and having a full black level, the first diameter corresponds to a 0.2° height based on a point 1.5 m apart, the circle transparent pattern includes a circle pattern having a maximum white level of the transparent display and an ambient surrounding the circle pattern having a maximum black level of the transparent display, and the second diameter is selected as one condition being that the second diameter corresponds to a 0.2° height based on a point 1.5 m apart, and that the second diameter covers an area including at least 500 pixels of the transparent display.

In one embodiment, when measuring luminance, the background further represents a circle black pattern, the light detector further measures a luminance of the circle black pattern passing through the circle transparent pattern displayed on the transparent display; and further comprising: calculating a criteria of the purity with the circle black luminance of the circle black pattern measured by the light detector; and evaluating an allowance error in which the calculated purity is decided as the purity of the transparent display when the criteria is satisfied, and the aligning the alignment axis is repeated when the criteria is not satisfied, the criteria is calculated by following equation.

$$\text{Criteria} = \frac{||L_{FW} - L_{CW}| - |L_{FK} - L_{CK}||}{|L_{FW} - L_{CW}|} \times 100 \leq 2(\%)$$

Here, $L_{FW}$ id the full white luminance, $L_{FK}$ id the full black luminance, $L_{CW}$ id the circle white luminance, and $L_{CK}$ id the circle black luminance.

In one embodiment, between the displacing the background and the light detector and the placing the transparent display, further comprising: measuring reference full white luminance of the full white pattern, a reference full black luminance of the full black pattern and a reference circle white luminance of the circle white pattern, without the transparent display; and calculating a reference purity of the background by equation 2.

$$P_{ref} = \frac{L_{CW,w/o} - L_{FK,w/o}}{L_{FW,w/o} - L_{FK,w/o}} \quad \text{(Equation 2)}$$

Here, $L_{FW,w/o}$ is the reference full white luminance, $L_{FW,w/o}$ is the reference full black luminance, and $L_{CW,w/o}$ is the reference circle white luminance.

The purity calculated by equation 1 is decided as a measured purity, and a new purity of the transparent display is calculated by the following equation 3.

$$\text{Purity}(\%) = \frac{P_{exp}}{P_{ref}} \times 100 \quad \text{(Equation 3)}$$

Here, $P_{exp}$ is the measured purity, and $P_{ref}$ is the reference purity.

The present invention can provide a new standard for evaluating a quality of a transparent display, the purity, considering the amount of the diffracted and scattered lights by transparent electrodes formed in the transparent display. According to the present invention, the purity is a new standard for evaluating the quality of a transparent display that is exactly proportional to the degree of the transparent property for the scene viewed by the observer through the transparent display. The purity is a new standard evaluating the quality of the transparent display which exactly defines how the background scene is seen by the observer through the transparent display. Further, the present invention can provide a system for evaluating the purity of a transparent display and a method for evaluating the purity. According to the present invention, unlike the haze and the clarity evaluation methods, the degree in which the background scene is affected by the transparent display can be accurately evaluated.

BRIEF DESCRIPTION OF THE DRAWINGS

The accompanying drawings, which are included to provide a further understanding of the invention and are incorporated in and constitute a part of this specification, illustrate embodiments of the invention and together with the description serve to explain the principles of the invention.

In the drawings.

DETAILED DESCRIPTION

Figure 1:
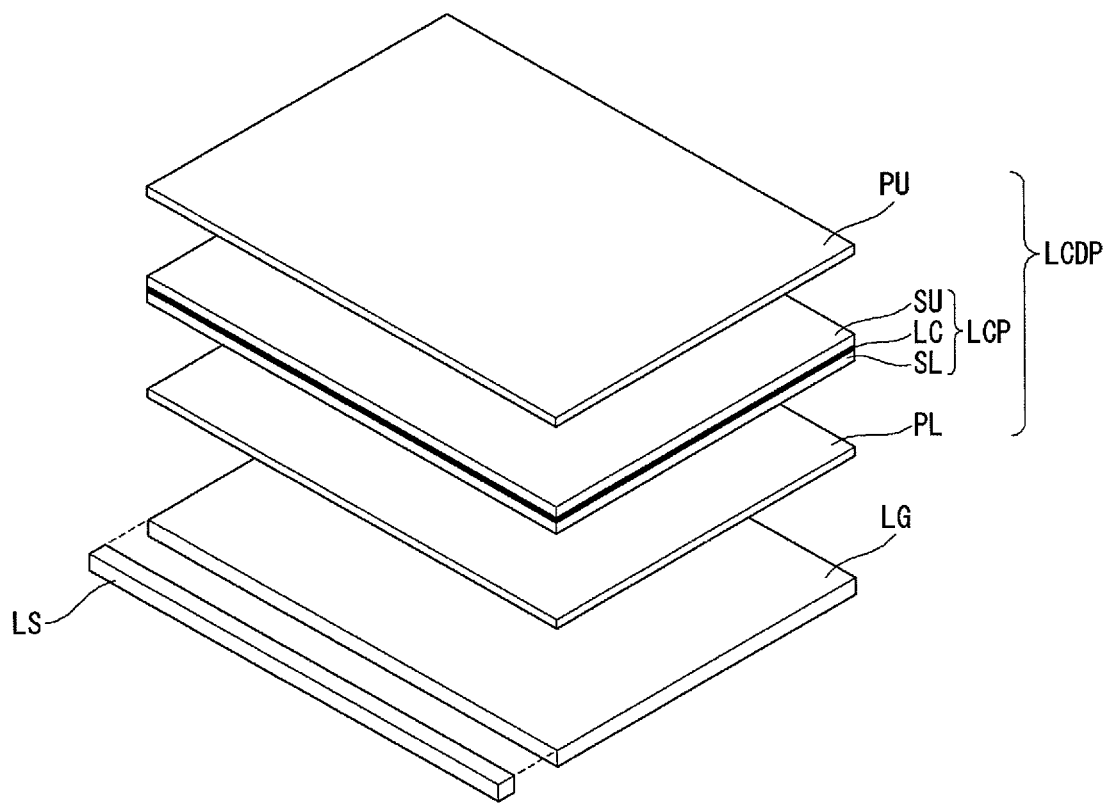
FIG. 1 is a perspective diagram illustrating the structure of a transparent display using a liquid crystal display.
Figure 2:
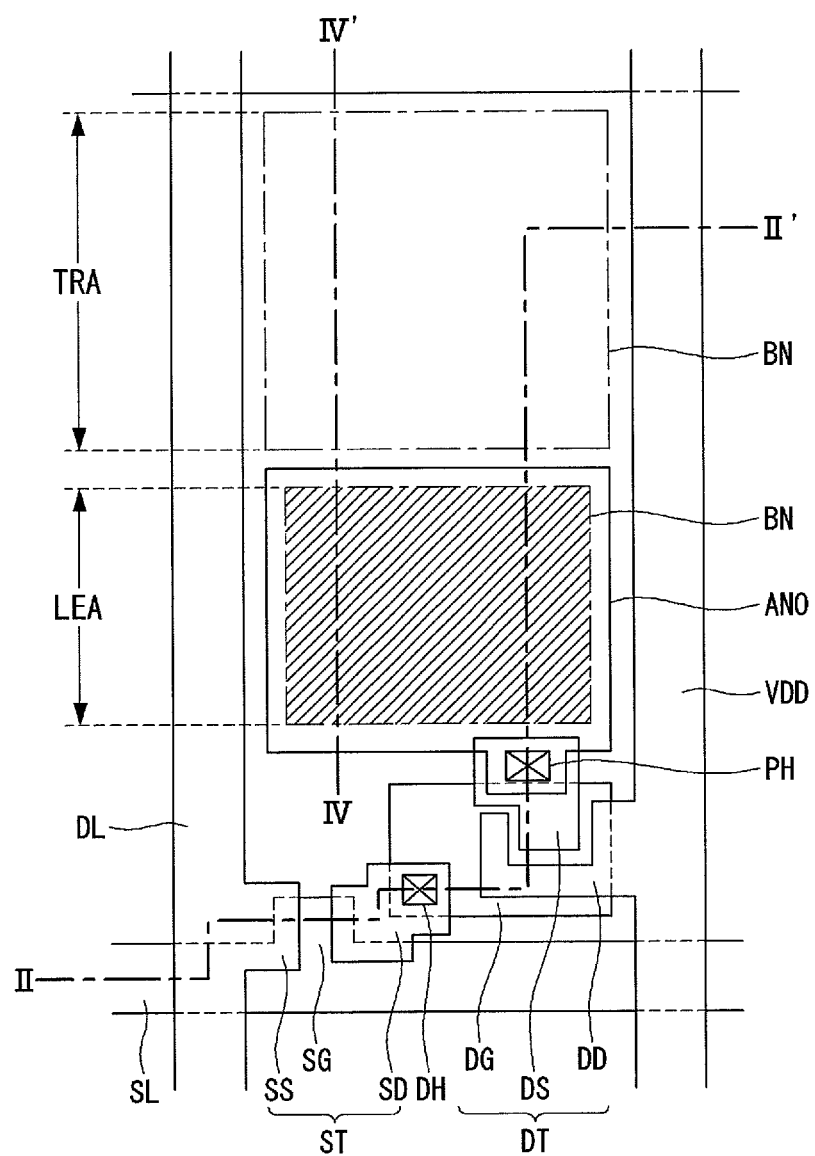
FIG. 2 is a plane view illustrating the structure of a transparent organic light emitting diode display.
Figure 3:
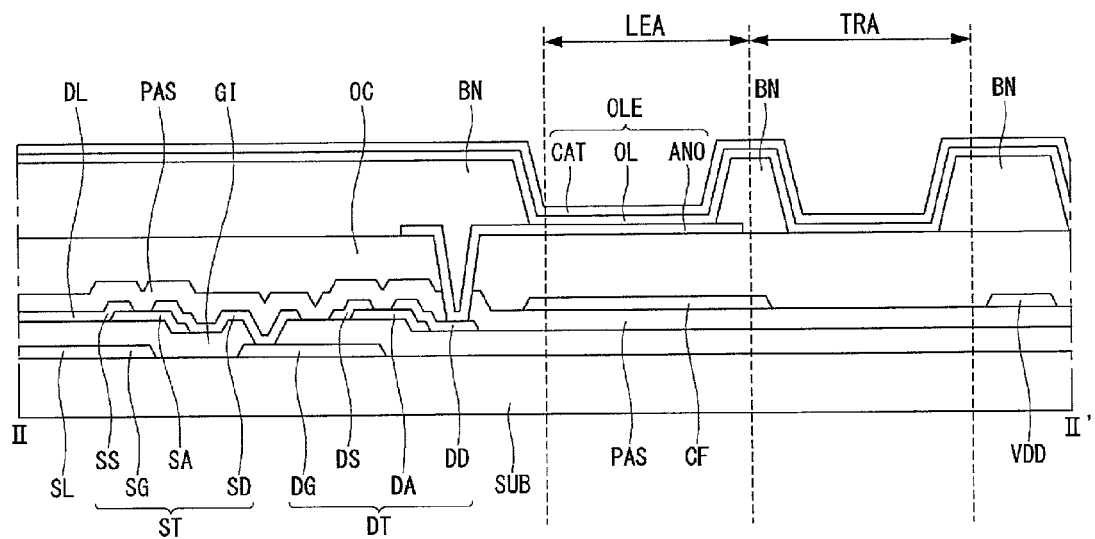
FIG. 3 is a cross sectional view illustrating the structure of a bottom emission type of transparent organic light emitting diode display along the cutting line I-I' of FIG. 2.
Figure 4:
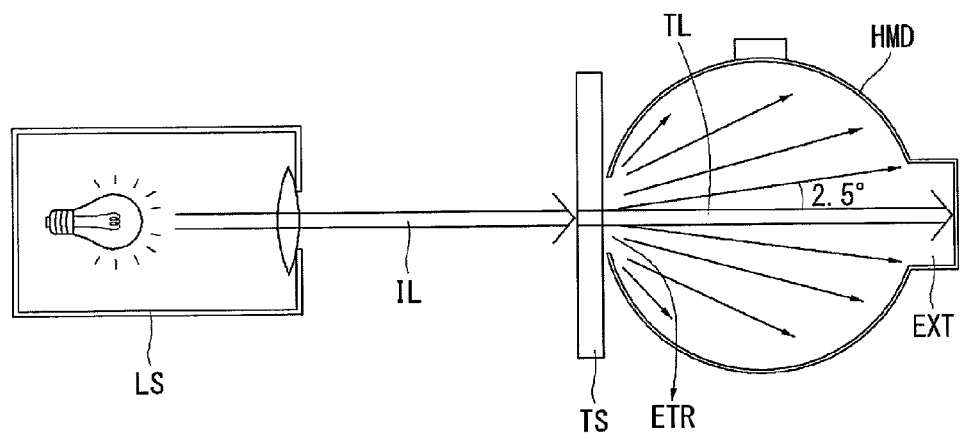
FIG. 4 is a schematic diagram illustrating the method for measuring the haze of a transparent display according to the related art.
Figure 5:
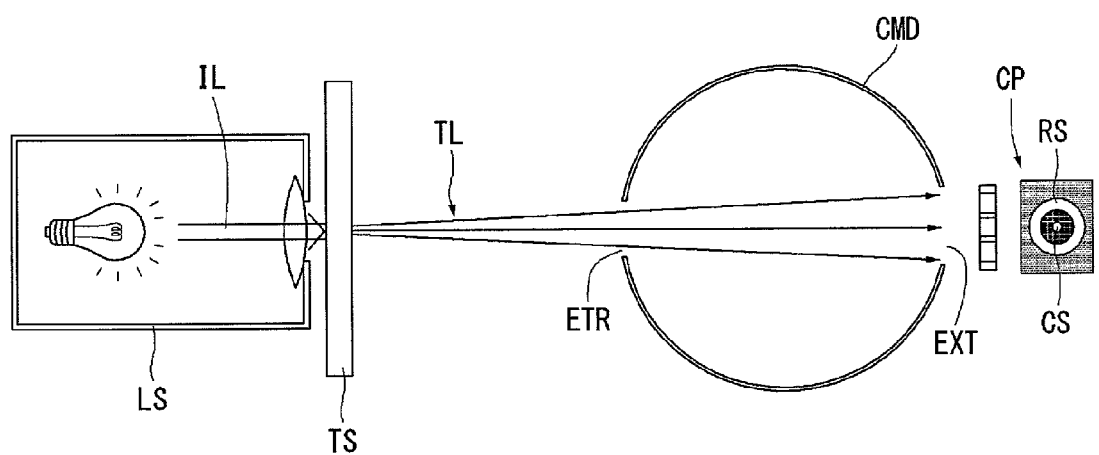
FIG. 5 is a schematic diagram illustrating the method for measuring the clarity of a transparent display according to the related art.

Referring to the attached figures, embodiments of the present invention will be explained. Like reference numerals designate like elements throughout the detailed description. However, the present invention is not restricted by these embodiments but can be applied to various changes or modifications without changing the technical spirit. In the following embodiments, the names of the elements are selected by considering the easiness for explanation so that they may be different from their actual names.

The present invention provides a new standard, the purity, for evaluating the quality of a transparent display. The descriptive definition of the purity can be defined as the degree of accuracy by which the observer and/or user can view the combined images at the permeate side of a transparent display.

To convert the descriptive definition into an objective numerical value, a mathematical definition of the purity is used. The mathematical definition of the purity can be viewed as a ratio of the luminance (or, brightness) changed by the diffraction and scattering to the maximum luminance passing though the transparent display by considering the black luminance of the background. This is defined as the following Equation 3.

$$\text{Purity}(\%) = \frac{L(\text{Brightness})_{pattern\text{-}passing}}{L(\text{Brightness})_{total\text{-}passing}} \times 100 \quad \text{(Equation 3)}$$

Here, the '$L(\text{Brightness})_{total\text{-}passing}$' is the maximum brightness of the background passing through the transparent display considering the black luminance of the background. It also can be referred to as the reference luminance or the reference brightness. Further, the '$L(\text{Brightness})_{pattern\text{-}passing}$' is the amount of luminance changed by the diffraction and/or scattering affections. It also means the 'changed luminance' by the diffraction and scattering of the light passing through a minimum pattern.

How the 'reference luminance' and the 'changed luminance' are measured, as in the above Equation 3, will be described referring to FIG. 6, which illustrates a method and a system for measuring the purity, the new standard for evaluating the quality of a transparent display will be explained. In particular, FIG. 6 is a schematic diagram illustrating a system for measuring the purity, the new standard for evaluating the quality of a transparent display, according to an embodiment of the present invention.

Figure 6:
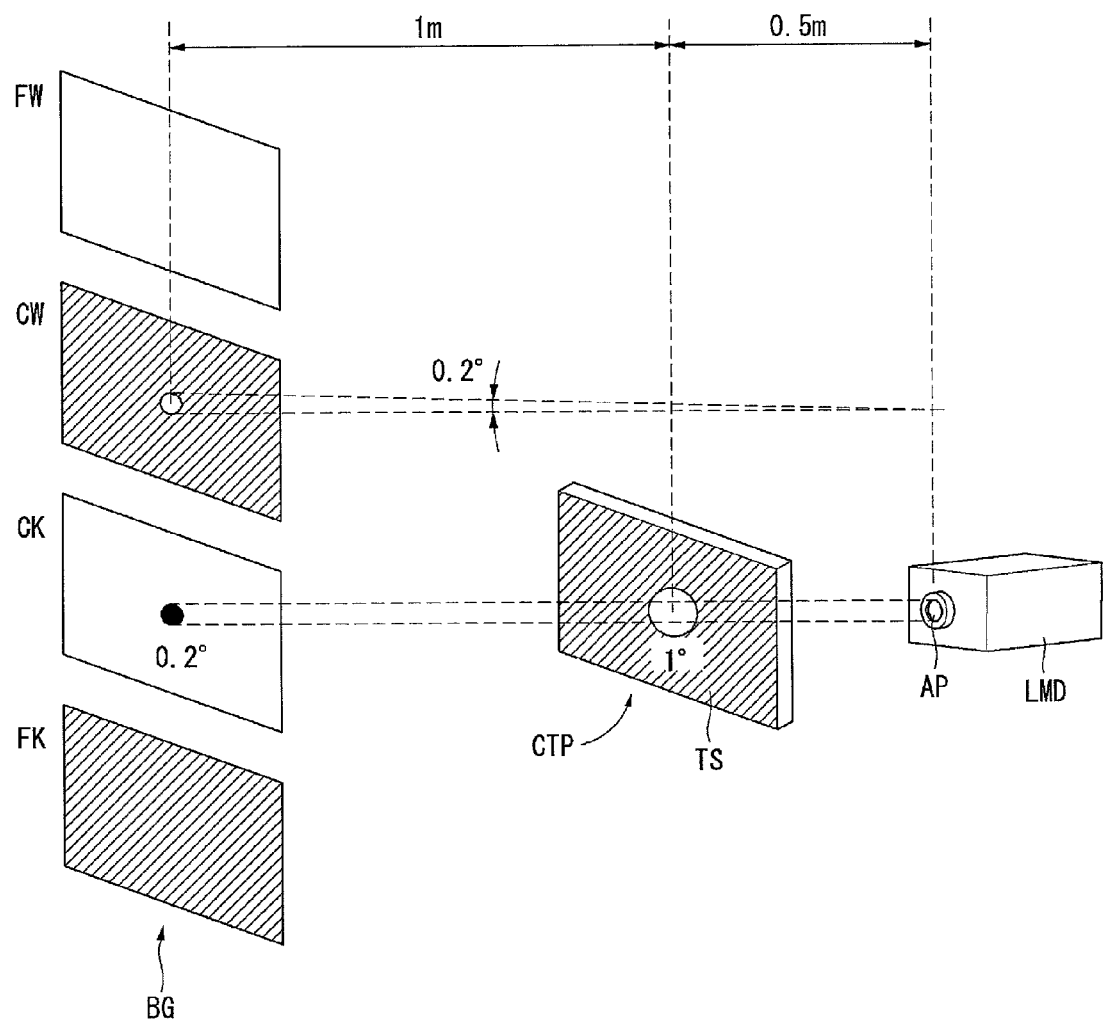
FIG. 6 is a schematic diagram illustrating a system for measuring the purity, the new standard for evaluating the quality of a transparent display, according to an embodiment of the present invention.

Referring to FIG. 6, the distance between a background BG and an observer is set to 1.5 m, as the standard distance in the optical measurement method. At the observer's position, a luminance detector LMD is located. A transparent display TS is disposed between the transparent display TS and the luminance detector LMD. The transparent display TS is located 0.5 m away from the luminance detector LMD. These location settings are decided by considering a representative environment for applying the transparent display by which an observer would view the scene of the background BG and the image represented on the transparent display, and by considering the general and standard conditions used when measuring the optical characteristics.

At the background BG, any one of a full white pattern FW, a circle white pattern CW, a circle black pattern CK and a full black pattern FK are selectively positioned. Here, the circle white pattern CW is a pattern in which one small circle having a pure white level is formed in the center of the background having a pure black level. Further, the circle black pattern CK is a pattern in which one small circle having a pure black level is formed in the center of the background having a pure white level.

The sizes of the circle white pattern CW and the circle black pattern CK correspond to the 0.2° height based on the center of the receiving lens AP of the light detector LMD spaced 1.5 m away from the patterns. Further, it is preferable that these patterns have the same shape and the same size as the aperture of the receiving lens AP. These conditions are decided by considering that the interference and affection of the light going into the light detector LMD from the circle patterns by the ambient light is minimized.

The size of 0.2° of the circle patterns is selected by considering that the minimum required height is 0.21° in which a person can exactly recognize a character or symbol from a distance of 1.5 m. Preferably, the size of the circle patterns and the aperture of the receiving lens AP of the light detector LMD are about 12.5 mm in diameter.

Further, a circle transparent pattern CTP is represented on the transparent display TS disposed between the background BG and the light detector LMD. The circle transparent pattern CTP having a maximum white level is positioned in the center of the background having a maximum black level of the transparent display. It is preferable that the center point of the circle transparent pattern CTP be aligned with the center point of the circle white pattern CW or the circle black pattern CK and the center point of the receiving lens AP of the light detector LMD.

In addition, the circle transparent pattern CTP preferably has a diameter corresponding to a height of 1° from the point 1.5 m distance. Here, the height 1° is selected as the circle area of the circle transparent pattern CTP that includes about 500 pixels. Therefore, the diameter of the circle transparent pattern CTP is not required to be just 1°. Rather, it would be satisfactory as long as at least 500 pixels are included in the area of the circle transparent pattern CTP and that the size of the circle transparent pattern CTP is larger than the sizes of the circle white pattern CW and the circle black pattern CK. In order to minimize interference by the ambient area surrounding the circle transparent pattern CTP, it is preferable that the background surrounding the circle transparent patter CTP have the maximum black level that can be represented by the transparent display.

The present invention relates to a system for evaluating how well the background scene BG passing through the transparent display TS can be recognized by the observer. Therefore, it is preferable that interference by ambient light should be minimized when measuring the purity. Preferably, the entire size of the background BG be much larger than the size of the transparent display TS. It is not required that a specific rational relationship between the size of the background BG and the size of the transparent display TS be defined. However, it is preferable that the size of the background BG is at least twice of the size of the transparent display TS.

Figure 7:
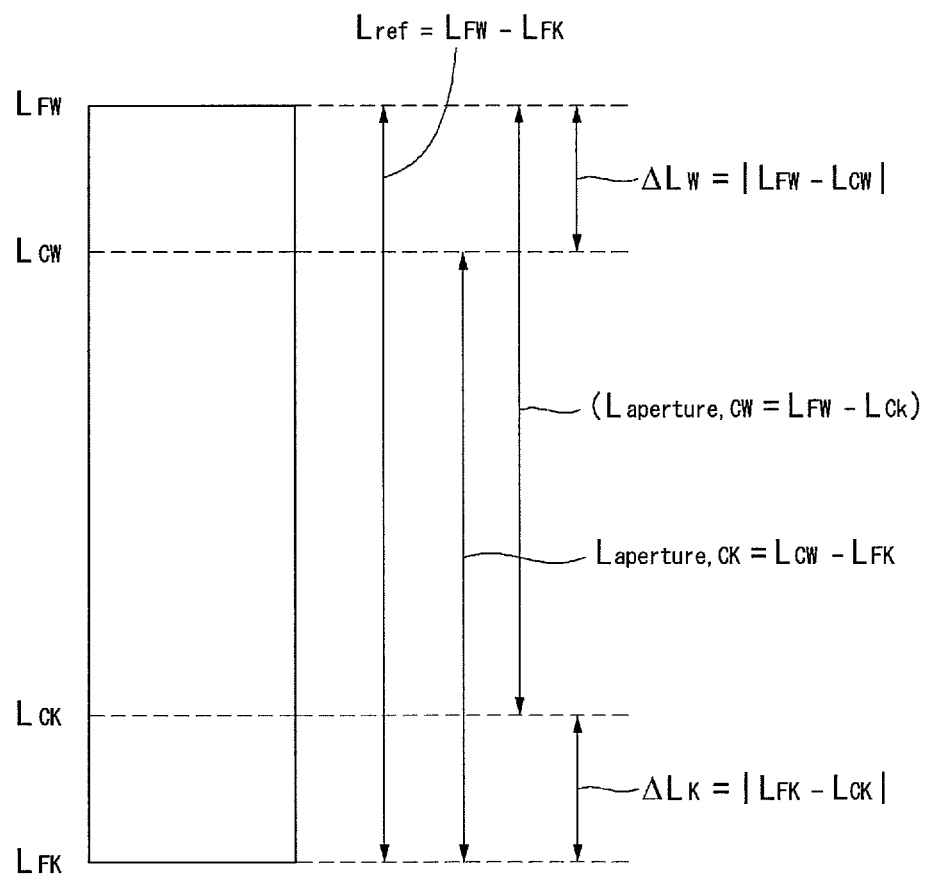
FIG. 7 is a diagram illustrating the luminescence of the representative patterns in a system for measuring the purity according to an embodiment of the present invention.

With the system shown in FIG. 6, the full white pattern FW is represented on the background BG, and the luminance (or brightness) is measured by the light detector LMD. This value is set as the full white luminance $L_{FW}$. Then, the full black pattern FK is represented on the background BG and the luminance is measured by the light detector LMD. This value is set as the full black luminance $L_{FK}$. Next, the circle white pattern CW is disposed at the background BG, and the luminance is measured by the light detector LIVID. This value is set as the circle white luminance $L_{CW}$. Lastly, the circle black pattern CK is positioned at the background BG, and the luminance is measured by the light detector LIVID. This value is set as the circle black luminance $L_{CK}$. Theses measured luminances are made up as shown in FIG. 7. In particular, FIG. 7 is a diagram illustrating the luminance of the representative patterns in a system for measuring the purity according to an embodiment of the present invention.

Referring to FIG. 7, the 'reference luminance $L_{ref}$' is the difference between the 'full white luminance $L_{FW}$' and the 'full black luminance $L_{FK}$', that is, $L_{FW}$-$L_{FK}$. Based on the 'reference luminance', the difference between the 'circle white luminance $L_{CW}$' and the 'full black luminance $L_{FK}$' is the 'changed luminance $L_{aperture,CK}$ of the circle black pattern CK' by the diffraction and scattering. In addition, the difference between the 'full white luminance $L_{FW}$' and the 'circle black luminance $L_{CK}$' is the 'changed luminance $L_{aperture,CW}$ of the circle white pattern CW' by the diffraction and scattering.

Using these four luminance values with Equation 3, the purity can be defined using the following Equation 4.

$$\text{Purity}(\%) = \frac{L_{aperture}}{L_{ref}} \times 100 = \frac{L_{CW} - L_{FK}}{L_{FW} - L_{FK}} \times 100 \qquad \text{(Equation 4)}$$

Here, the $L_{CW}$ is the circle white luminance, the $L_{FK}$ means the full black luminance, and the $L_{FW}$ means the full white luminance.

As for another expression, the purity can be defined using the following Equation 5.

$$\text{Purity}(\%) = \left(1 - \frac{\Delta L_W}{L_{ref}}\right) \times 100 = \left(1 - \frac{L_{FW} - L_{CW}}{L_{FW} - L_{FK}}\right) \times 100 \qquad \text{(Equation 5)}$$

Here, $\Delta L_W$ is the amount of luminance distorted by the diffraction and the scattering, as the difference (absolute value) between the full white luminance $L_{FW}$ and the circle white luminance $L_{CW}$. In addition, $L_{CW}$ is the circle white luminance, $L_{FK}$ is the full black luminance, and $L_{FW}$ is the full white luminance.

The difference between the 'full white luminance $L_{FW}$' and the 'circle white luminance $L_{CW}$', as the distorted luminance of the light from the circle white pattern CW by the transparent display, can be defined as $\Delta L_W$. The difference (absolute value) between the 'full black luminance $L_{FK}$' and the 'circle black luminance $L_{CK}$', as the distorted luminance of the light from the circle black pattern CK by the transparent display, can be defined as $\Delta L_K$. Here, as for the same transparent display, this distorted luminance should be the same value. That is, ideally, $\Delta L_W$ should be same with $\Delta L_K$.

To make $\Delta L_W$ to be the same as $\Delta L_K$, the centers of the circle patterns in the background BG should be exactly aligned with the center of the receiving lens AP of the light detector LMD. Actually, in the system and the method explained in the FIG. 6, with the four measured luminances, when the difference between $\Delta L_W$ and $\Delta L_K$ is less than 2% tolerance, then the measurement for the purity is correctly performed. That is, the measured values are reliable.

In other words, when the following Equation 6 is satisfied, the measuring system is correctly aligned, and the measuring error is within the allowance error (tolerance).

$$\text{Criteria} = \frac{\Delta L_W - \Delta L_K}{\Delta L_W} \times 100 = \frac{|L_{FW} - L_{CW}| - |L_{FK} - L_{CK}|}{|L_{FW} - L_{CW}|} \le 2(\%) \quad \text{(Equation 6)}$$

Here, $\Delta L_W$ is the absolute difference between the full white luminance $L_{FW}$ and the circle white luminance $L_{CW}$, $\Delta L_K$ is the absolute difference between the full black luminance $L_{FK}$ and the circle black luminance $L_{CK}$, $L_{FW}$ is the full white luminance, $L_{FK}$ is the full black luminance, $L_{CW}$ is the circle white luminance, and $L_{CK}$ is the circle black luminance.

Using the purity, the new standard for evaluating the quality of a transparent display, it is possible to have very exact evaluating values that are proportional to the actual clearness and luminance of the background scene that would be recognized by the observer. In more detail, according to the related art, even though two transparent displays have the same clarity value, the observer's ability to view the background through these two transparent displays would be very different due to a small difference in the haze values. According to embodiments of the present invention, the purity values would be very different for these same two transparent displays. In another situation, two transparent displays of which the clarities are similar to each other, the observer's recognition of one display having better haze value may actually be worse than the other display having a worse haze value. In that situation, according to an embodiment of the present invention, the purity values would be proportional to the degree of the observer's recognition.

That is, it is impossible to obtain an objective and exact evaluation with the clarity and/or the haze evaluation methods. In contrast, it is possible to provide an objective and exact evaluation standard for the quality of a transparent display using the purity standard.

Figure 8:
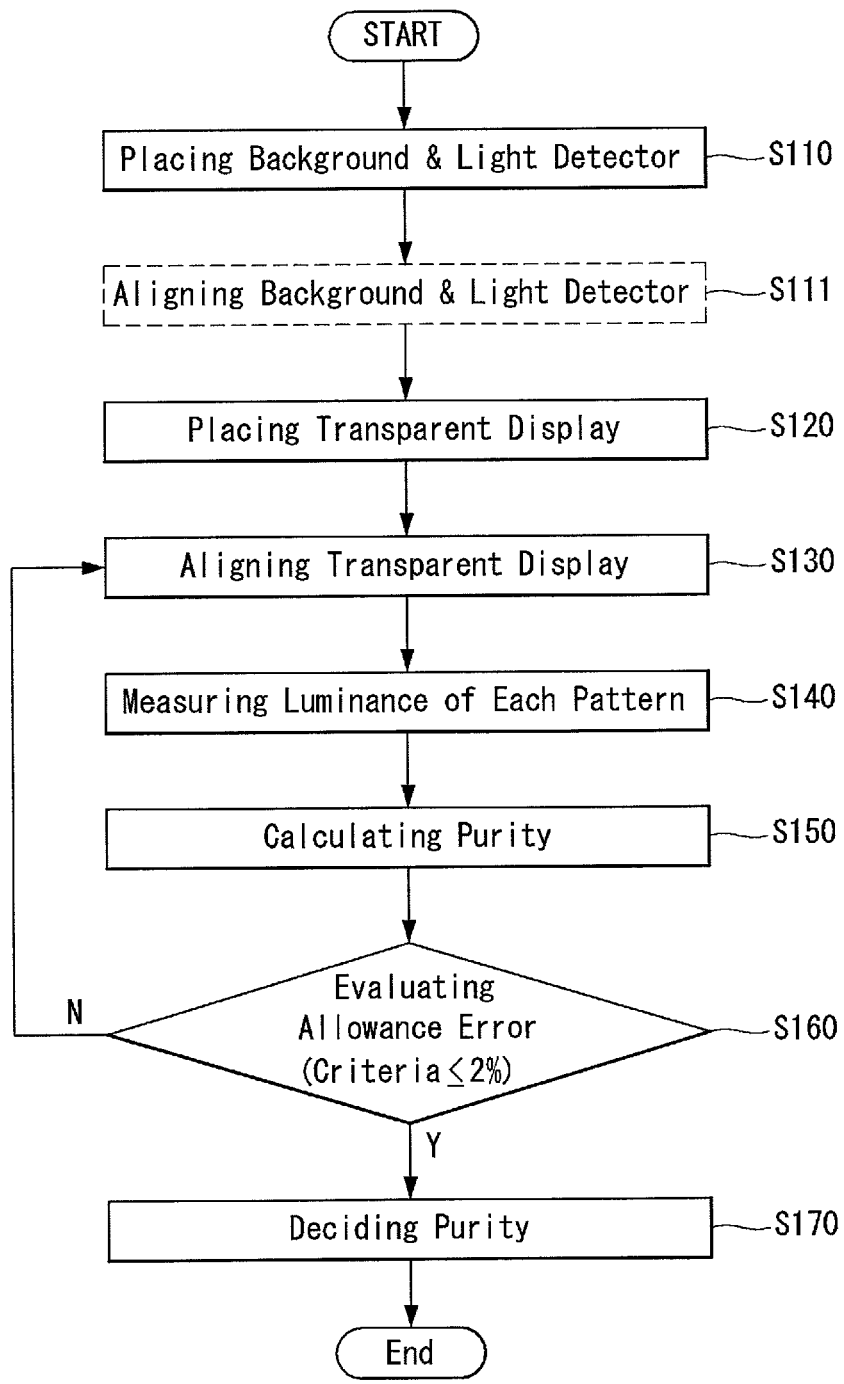
FIG. 8 is a flow chart illustrating a method for measuring the purity, which is a new standard for evaluating the quality of a transparent display, according to an embodiment of the present invention.

Hereinafter, referring to FIG. 8, a method for measuring the purity according to an embodiment of the present invention will be explained in detail. FIG. 8 is a flow chart illustrating a method for measuring the purity, the new standard for evaluating the quality of a transparent display, according to an embodiment of the present invention.

A background BG is placed as representing any one of the full white pattern FW, the circle white pattern CW, the circle black pattern CK, and the full black pattern FK is selectively represented. A light detector LMD is placed at a position spaced 1.5 m away from the background BG (referring to S110).

By using a properly designed jig for measurement when installing the background BG and the light detector LMD, it is possible to align the center of the circle white pattern CW and/or the circle black pattern CK with the center of the receiving lens AP of the light detector LMD. When the measuring system is designed as a portable system, a step may be provided for using a specific alignment device for aligning the center of the circle white pattern CW and/or the circle black pattern CK with the center of the receiving lens AP of the light detector LMD (referring to S111). In FIG. 8, the step of S111 may be optional and is shown as a dotted line.

A transparent display TS is placed between the background BG and the light detector LMD. Specifically, the transparent display TS can be located at a position spaced 0.5 m apart from the light detector LMD (S120). Since the transparent display TS may have a different size, even though a jig is used to install the transparent display TS, it may be difficult to align the center of the transparent display TS exactly with the center of the circle white pattern CW and/or the circle black pattern CK and to the center of the receiving lens AP of the light detector LMD.

When installing the transparent display TS it is preferable that the alignment is performed correctly. For example, the alignment process can be performed using the center point of the transparent display TS. However, it may be more accurate to perform the alignment process using the center point of the circle transparent pattern CTP displayed at the center of the transparent display TS. For example, after the circle transparent pattern CTP is represented at the center of the transparent display TS, then the alignment process can be performed using the center point of the circle transparent pattern CTP by moving the circle transparent pattern CTP on the transparent display TS. There may be various methods for conducting the alignment process. One detailed method will be explained later (referring to S130).

The circle transparent pattern CTP is displayed at the center of the transparent display TS. The full white pattern FW, the circle white pattern CW, the circle black pattern CK and/or the full black pattern FK are sequentially displayed on the background BG. Using the light detector LMD, the luminance for each of these patterns is measured. That is, the measured values are the full white luminance $L_{FW}$, the full black luminance $L_{FK}$, the circle white luminance $L_{CW}$ and the circle black luminance $L_{CK}$ (S140).

Using the Equations 4 and 5, the purity can be calculated (S150). Further, using Equation 6, it is evaluated whether the measurement error of the purity acquired in the step S150 is within the allowance error or not. When the error evaluation result is outside of the allowance error, it may mean that the center of the circle transparent pattern CTP is not properly aligned with the center of the circle white pattern CW and/or the circle black pattern CK positioned at the background BG and the center of the receiving lens AP of the light detector LMD. In that case, the method returns back to step S130, and the alignment process of the transparent display TS is repeated until the error evaluating result is within the allowance error (according to the Equation 6) (S160). When the error evaluation result obtained at step S160 is within the allowance error, the purity of the transparent display TS is decided as the calculated value in step S150 (S170).

In the explanation of embodiments of the present invention, the error evaluation step using the Equation 6 is necessarily included. However, when the measuring system is ensured to be within the alignment allowance error, this error evaluation step can be omitted. In the actual manufacturing process of the transparent displays, the purity is measured at the quality conformation step. In that situation, a plurality of the transparent display TS having the same size are repeatedly checked. In that situation, it is preferable that the allowance error evaluation process be performed when the periodical inspection is performed for the manufacturing system.

Until now, the explanation is based on the condition in which the patterns disposed at the background BG have the pure full gray scale level and the luminance corresponds to these scale levels. That is, the full white pattern has 100% luminance and the full black pattern has 0% luminance. For the circle white pattern, the ambient has the full black luminance of 0% and the circle pattern has 100% luminance. In addition, for the circle black pattern, the ambient has the full white luminance of 100% and the circle pattern has 0% luminance.

In that situation, the background BG should be prepared as a standardized pattern. When a standardized pattern is not prepared, the measured purity cannot be decided as an exact value of the purity. For example, when the size of the background BG satisfying the standard is 20 inches and the size of the transparent display TS is larger than 40 inch, it is hard to correctly measure the purity value. For example, a properly sized standard background BG should be prepared. Much time may be required for preparing a new standard background and evaluating whether the background BG satisfies the standard.

Therefore, in a preferred embodiment of the present invention, a method is provided for measuring the purity exactly, even though the patterns disposed at the background BG do not satisfy the pure full gray scale levels. The purity measuring system according to a preferred embodiment of the present invention has the same structure as the system mentioned above. The difference being that the white level may not be 100% and/or the black level may not be 0% when the patterns are disposed at the background BG.

In a preferred embodiment of the present invention, after installing the background BG and the light detector LMD, the reference luminance $L_{ref}$ is firstly measured before installing the transparent display TS. In order to measure the reference luminance $L_{ref}$ without the transparent display TS, the full white pattern FW, the full black pattern FK, the circle white pattern CW and the circle black pattern CK are disposed sequentially. Then, without the transparent display TS, the luminance of the patterns including the reference full white luminance $L_{FW,w/o}$, the reference full black luminance $L_{FK,w/o}$, the reference circle white luminance $L_{CW,w/o}$, and the reference circle black luminance $L_{CK,w/o}$ are measured. In some instances, the reference circle black luminance $L_{CK,w/o}$ may not be measured. Here, 'w/o' means the condition in which the transparent display TS is not installed. Then, the reference purity $P_{ref}$ can be acquired as the following Equation 7.

$$P_{ref} = \frac{L_{CW,w/o} - L_{FK,w/o}}{L_{FW,w/o} - L_{FK,w/o}} \quad \text{(Equation 7)}$$

Here, $L_{FW,w/o}$ is the reference full white luminance, $L_{FK,w/o}$ is the reference full black luminance, and $L_{CW,w/o}$ is the reference circle white luminance.

After that, the transparent display TS is installed between the background BG and the light detector LMD, and the measuring of the purity $P_{exp}$ is calculated. As mentioned above, displaying the full white pattern FW, the full black pattern FK, the circle white pattern CW and the circle black pattern CK are displayed on the background BG, the luminance including the full white luminance $L_{FW,w/}$, the full black luminance $L_{FK,w/}$, the circle white luminance $L_{CW,w/}$ and the circle black luminance $L_{CK,w/}$ are measured, respectively. In some instances, the circle black luminance $L_{FK,w/}$ may be not measured. Here, 'w/' means the condition in which the transparent display TS is installed. Then, the measured purity $P_{exp}$ using the background BG can be acquired as the following Equation 8.

$$P_{exp} = \frac{L_{CW,w/} - L_{FK,w/}}{L_{FW,w/} - L_{FK,w/}} \quad \text{(Equation 8)}$$

Here, $L_{FW,w/}$ is the measured full white luminance of the transparent display TS, $L_{FK,w/}$ is the measured full black luminance of the transparent display TS, and $L_{CW,w/}$ is the measured circle white luminance of the transparent display TS.

In the above preferred embodiment of the present invention, unlike the former explained embodiment, the measured purity cannot be decided as the purity of the transparent display. The reason being that the measured purity is not acquired by considering the background. Therefore, with considering the background, it is possible to decide the correct purity. That is, using the reference purity $P_{ref}$ and the measured purity $P_{exp}$, the purity can be acquired using the following Equation 9.

$$\text{Purity}(\%) = \frac{P_{exp}}{P_{ref}} \times 100 \quad \text{(Equation 9)}$$

Here, $P_{ref}$ is the reference purity without the transparent display, and $P_{exp}$ is the measured purity with the transparent display.

In a preferred embodiment of the present invention, a method is provided for measuring the purity when the patterns displayed on the background BG do not have the pure full gray scale level. For example, when the background is configured using a flat panel display such as a liquid crystal display, an organic light emitting diode display or a plasma display, the gray scale of the patterns represented on the flat panel display may not be in compliance with the standard gray scale. In that case, as mentioned in the preferred embodiment, it is preferable that the purity be decided by using the reference purity and the measured purity.

Figure 9:
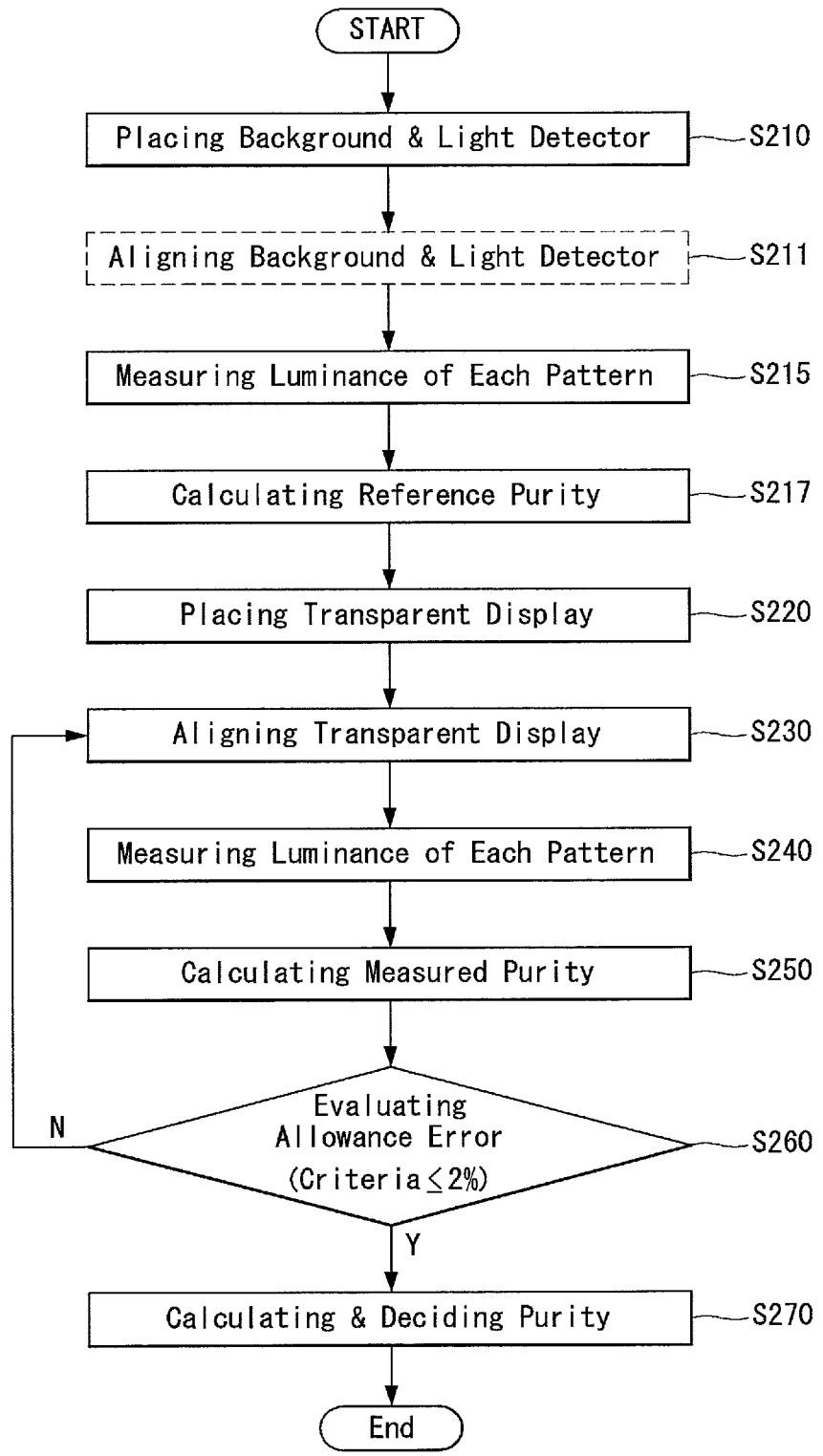
FIG. 9 is a flow chart illustrating a method for measuring the purity, which is a new standard for evaluating the quality of a transparent display, according to an embodiment of the present invention.

Hereinafter, referring to FIG. 9, we will explain about the method for measuring the purity according to the preferred embodiment of the present invention, in detail. FIG. 9 is a flow chart illustrating a method for measuring the purity the new standard evaluating the quality of the transparent display, according to a preferred embodiment of the present invention.

A background BG is placed for selectively displaying any one of the full white pattern FW, the circle white pattern CW, the circle black pattern CK and the full black pattern FK. A light detector LMD is placed at the position which is 1.5 m away from the background BG (FIG. 9).

By using a properly designed jig for measurement when installing the background BG and the light detector LMD, it is possible to align the center of the circle white pattern CW and/or the circle black pattern CK with the center of the receiving lens AP of the light detector LMD. In the situation that the measuring system is designed as a portable system, a step may be provided for aligning the center of the circle white pattern CW and/or the circle black pattern CK with the center of the receiving lens AP of the light detector LMD using a specific alignment device (S211). In FIG. 9, the step of S211 may be optional, thus it is shown as a dotted line.

On the background BG, the full white pattern FW, the circle white pattern CW, the circle black pattern CK, and/or the full black pattern FK are sequentially displayed. Each luminance of each pattern is measured using the light detector LMD. That is, the reference full white luminance $L_{FW,w/o}$, the reference full black luminance $L_{FK,w/o}$, the reference circle white luminance $L_{CW,w/o}$, and the reference circle black luminance $L_{CK,w/o}$ are measured (S215). Using the Equation 7, the reference purity $P_{ref}$ is calculated (S217).

A transparent display TS is placed between the background BG and the light detector LMD. Particularly, the transparent display TS can be located at a position spaced 0.5 m away from the light detector LIVID (S220). As the transparent display TS may have a different size, even when using a jig, it may be difficult to align the center of the transparent display TS exactly with the center of the circle white pattern CW and/or the circle black pattern CK and with the center of the receiving lens AP of the light detector LIVID, just by installing the transparent display TS.

When installing the transparent display TS it is preferable that the alignment is performed correctly. For example, the alignment process can be performed using the center point of the transparent display TS. However, it may be more accurate to perform the alignment process using the center point of the circle transparent pattern CTP displayed at the center of the transparent display TS. For example, after the circle transparent pattern CTP is represented at the center of the transparent display TS, then an alignment process can be performed using the center point of the circle transparent pattern CTP by moving the circle transparent pattern CTP on the transparent display TS. There may be various methods for conducting the alignment process. One detailed method will be explained later (S230).

The circle transparent pattern CTP is displayed at the center of the transparent display TS. The full white pattern FW, the circle white pattern CW, the circle black pattern CK and/or the full black pattern FK are sequentially displayed on the background BG. Using the light detector LIVID, the luminance of each of these patterns is measured. That is, the measured values are the measured full white luminance $L_{FW,w/}$, the measured full black luminance $L_{FK,w/}$, the measured circle white luminance $L_{CW,w/}$ and the measured circle black luminance $L_{CK,w/}$ (referring to S240).

Using the Equation 8, the measured purity $P_{exp}$ may be calculated (S250). Further, using Equation 6, it is evaluated whether the measurement error of the purity acquired in the step S250 is within the allowance error or not. When the error evaluation result is outside of the allowance error, it may indicate that the center of the circle transparent pattern CTP is not aligned with the center of the circle white pattern CW and/or the circle black pattern CK disposed at the background BG and with the center of the receiving lens AP of the light detector LMD. In that situation, the method returns back to the step S230, and the alignment process of the transparent display TS is repeated until the error evaluating result is within the allowance error (according to the Equation 6) (S260).

When the error evaluation result obtained at the step S260 is within the allowance error, substituting the measured purity $P_{exp}$ acquired in the step S250 and the reference purity $P_{ref}$ acquired in the step 217 into the Equation 9, the purity of the transparent display TS is decided (referring to S270).

Figure 10:
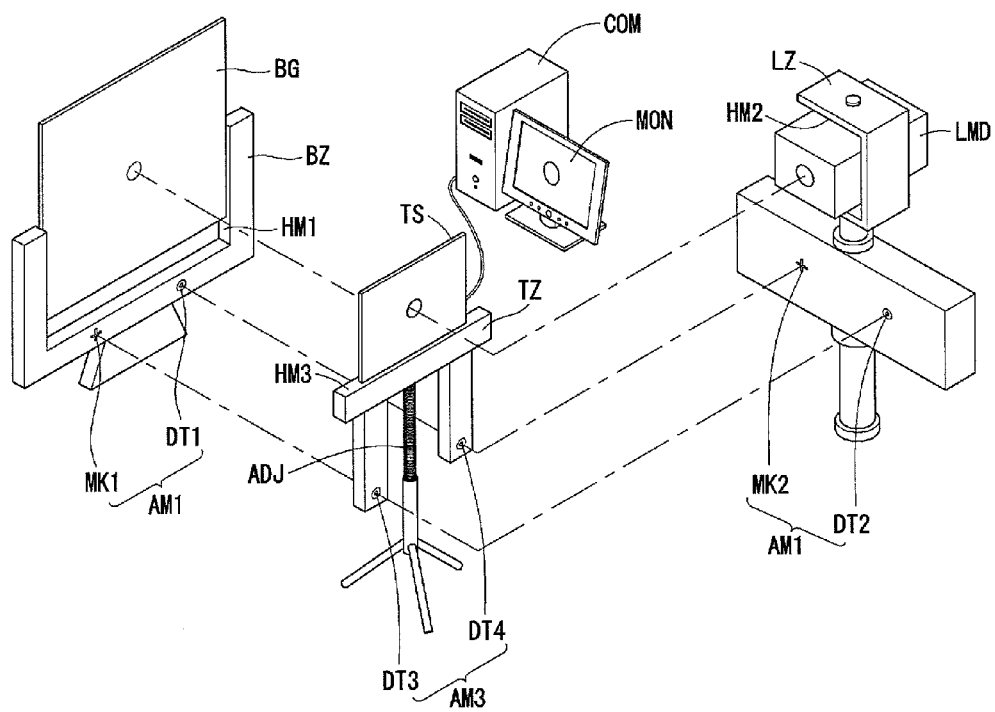
FIG. 10 is a perspective view illustrating a system for measuring the purity according to an embodiment of the present invention.

Hereinafter, referring to FIG. 10, an alignment method for ensuring the accuracy of the measurement of the purity according to an embodiment of the present invention will be explained. FIG. 10 is a perspective view illustrating a system for measuring the purity according to an embodiment of the present invention. While FIG. 6 is a schematic diagram illustrating a system for measuring the purity, FIG. 10 is a diagram illustrating a system for measuring the purity. The measuring system and the alignment process are not restricted by this embodiment.

A background jig BZ for installing a background BG may be located at a point. A display configured to represent any one of the full white pattern FW, the circle white pattern CW, the circle black pattern CK, and the full black pattern FK may be installed at the background jig BZ. Any one panel or sheet having any one of the full white pattern FW, the circle white pattern CW, the circle black pattern CK, and the full black pattern FK may be selectively installed at the background jig BZ. For example, the background jig BZ may include a first holding means HM1 for assembling and/or disassembling the panel or sheet. Further, the background jig BZ may comprise a first alignment means AM1 for alignment in the system. For example, the first alignment means AM1 may include a first align mark MK1 having a '+' shape and/or a first detector DT1 for recognizing the first align mark MK1.

At a position 1.5 m away from the background jig BZ, a light detector jig LZ for installing a light detector LIVID can be placed. The light detector jig LZ may comprise a second holding means HM2 for installing the light detector LMD and a second alignment means AM2. The second alignment means AM2 may include a second detector DT2 for recognizing the first align mark MK1 of the first alignment means AM1. Otherwise, The second alignment means AM2 may include a second align mark MK2 which can be recognized by the first detector DT1 of the alignment means AM1.

Using the first alignment means AM1 and the second alignment means AM2 included in the background zig BZ and the light detector zig LZ, respectively, the center of the background BG can be aligned with the center of the lens of the light detector LIVID. After locating the background jig BZ and the light detector jig LZ at their respective positions, and aligning the first alignment means AM1 with the second alignment means AM2, the background BG can be set on the background jig BZ and the light detector LIVID can be set on the light detector jig LZ. Then, automatically, the background BG can be aligned with the light detector LMD. That is, the alignment axis of the system for measuring the purity is established.

A transparent display jig TZ is placed between the background zig BZ and the light detector jig LZ. Especially, the transparent display jig TZ is located at a position 0.5 m away from the light detector jig LZ. The transparent display jig TZ may include a third holding means HM3 for assembling and/or disassembling a transparent display TS. It is preferable that a system for measuring the purity according to an embodiment of the present invention can measure various sizes of the transparent display TS. Therefore, it is preferable that the third holding means HM3 of the transparent display jig TZ may be configured to hold various sizes of the transparent display TS.

As the size of the transparent display TS is not fixed, the position of the center point of the transparent display TS is not fixed. It is possible to set the horizontal position of the center point of various transparent displays TS on a known point. The horizontal coordinate of the center point of the transparent display TS can be set on the horizontal coordinates of the center point of the background BG or the light detector LMD. Therefore, the transparent display jig TZ may include a third alignment means AM3 for aligning the transparent display jig TZ. For example, the third alignment means AM3 may have a third detector DT3 for recognizing the first alignment mark MK1 and a fourth detector DT4 for recognizing the second alignment mark MK2. As the vertical coordinate of the center of the transparent display TS may be varied, it is preferable that the transparent display jig TZ may include an adjuster ADJ for controlling the height of the transparent display TS.

After installing the transparent display TS on the transparent display jig TZ, a circle transparent pattern CTP can be displayed on the center of the transparent display TS. To do so, a computer COM may be connected to the transparent display TS for providing the display information corresponding to the circle transparent pattern CTP. In this instance, the computer COM may have a program for adjusting the location of the circle transparent pattern CTP on the transparent display TS. Further, a monitor MON for confirming the position of the circle transparent pattern CTP on the transparent display TS may be included. Observing the circle transparent pattern CTP through the monitor MON, the center position of the circle transparent pattern CTP can be controlled and/or adjusted to be aligned onto the center of the transparent display TS.

There may be various methods for adjusting the height of the transparent display TS. For example, a LASER tool can be installed at the center of the background BG (or the center of the patterns of the background BG) and then the LASER beam can be radiated to the transparent display TS. Then, it is possible to check whether the center of the circle transparent pattern CTP is aligned onto the center of the background BG (or the alignment axis of the system). Of course, even though there are many other methods, here we will not explain.

Changing the patterns on the background BG and measuring each luminance, the errors can be calculated by the Equation 6. When the error is outside of the allowance error range, the position of the circle transparent pattern CTP should be changed as to be exactly aligned onto the alignment axis of the system.

For the situation that the diagonal size of the transparent display TS is smaller than 10 inches, the purity can be acquired by measuring on one central portion of the transparent display TS. However, for the case that the diagonal size of the transparent display TS is larger than 50 inches, it is required to check and/or evaluate the purities on various positions over the whole surface of the transparent display TS that are the same or similar. To do so, the circle transparent pattern CTP should be moved over the transparent display TS, and the moved center point of the circle transparent pattern CTP should be re-aligned onto the alignment axis of the system. After that the purity is decided again and again.

Until now, a measuring system and an alignment process have been explained with a simple model. However, with an automation system, it is possible to establish an automatic system for evaluating and/or measuring the purity more easily, quickly and exactly.

While the embodiments of the present invention have been described in detail with reference to the drawings, it will be understood by those skilled in the art that the invention can be implemented in other specific forms without changing the technical spirit or essential features of the invention. Therefore, it should be noted that the forgoing embodiments are merely illustrative in all aspects and are not to be construed as limiting the invention. The scope of the invention is defined by the appended claims rather than the detailed description of the invention. All changes or modifications or their equivalents made within the meanings and scope of the claims should be construed as falling within the scope of the invention.

What is claimed is:

1. A system for evaluating a quality of a transparent display, the system comprising:
    a background including any one of a full white pattern, a full black pattern, and a circle white pattern;
    a light detector positioned a first distance away from the background and configured to measure luminance of the full white pattern, the full black pattern and the circle white pattern; and
    a circle transparent pattern displayed on the transparent display by passing light from at least one of the full white pattern, the full black pattern and the circle white pattern, wherein the transparent display is positioned between the background and the light detector and at a position with a second distance away from the light detector,
    wherein a purity of the transparent display is calculated by the following equation 1:

$$\text{Purity}(\%) = \frac{L_{CW} - L_{FK}}{L_{FW} - L_{FK}} \times 100 \quad \text{(Equation 1)}$$

and wherein $L_{FW}$ is a full white luminance of the full white pattern, $L_{FK}$ is a full black luminance of the full black pattern, and $L_{CW}$ is a circle white luminance of the circle white pattern as measured by the light detector through the transparent display, respectively.

2. The system according to claim 1, wherein the first distance is 1.5 m and the second distance is 0.5 m.

3. The system according to claim 1, wherein the circle white pattern includes a circle pattern having a first diameter and a full white level, and an ambient surrounding the circle pattern and having a full black level, and
    wherein the first diameter corresponds to a 0.2° height based on a point 1.5 m away from the light detector.

4. The system according to claim 1, wherein the circle transparent pattern includes a circle pattern having a maximum white level of the transparent display and an ambient surrounding the circle pattern having a maximum black level of the transparent display, and
    wherein a diameter of the circle pattern corresponds to a 0.2° height based on a point 1.5 m away from the light detector, and covers an area including at least 500 pixels of the transparent display.

5. The system according to claim 1, wherein a shape and a size of the circle white pattern and a receiving lens of the light detector are the same, and
    a center of the circle white pattern, a center of the circle transparent pattern, and a center of the receiving lens are aligned in a straight line.

6. The system according to claim 1, wherein the background further represents a circle black pattern,
    wherein the light detector is configured to measure a luminance of the circle black pattern passing through the circle transparent pattern displayed on the transparent display, and wherein a criteria of the purity is calculated by the following equation:

$$\text{Criteria} = \frac{|L_{FW} - L_{CW}| - |L_{FK} - L_{CK}|}{|L_{FW} - L_{CW}|} \times 100 \le 2(\%)$$

wherein $L_{FW}$ is the full white luminance, $L_{FK}$ is the full black luminance, $L_{CW}$ is the circle white luminance, and $L_{CK}$ is the circle black luminance.

7. The system according to claim 6, wherein the circle black pattern includes a circle pattern with a full black level having a first diameter and an ambient with a full white level, and
wherein the first diameter corresponds to a 0.2° height based on a point 1.5 m away from the light detector.

8. The system according to the claim 1, wherein the light detector is further configured to measure a reference full white luminance of the full white pattern, a reference full black luminance of the full black pattern and a reference circle white luminance of the circle white pattern, without the transparent display being positioned between the light detector and the background,
wherein a reference purity is calculated by following equation 2:

$$P_{ref} = \frac{L_{CW,w/o} - L_{FK,w/o}}{L_{FW,w/o} - L_{FK,w/o}} \quad \text{(Equation 2)}$$

wherein, $L_{FW,w/o}$ is the reference full white luminance, $L_{FK,w/o}$ is the reference full black luminance, and $L_{CW,w/o}$ is the reference circle white luminance, and
wherein the purity calculated by the equation 1 is decided as a measured purity,
wherein a new purity of the transparent display is calculated by the following equation 3:

$$\text{Purity}(\%) = \frac{P_{exp}}{P_{ref}} \times 100 \quad \text{(Equation 3)}$$

wherein $P_{exp}$ is the measured purity, and $P_{ref}$ is the reference purity.

9. A method for evaluating a quality of a transparent display, the method comprising:
positioning a background configured to represent any one of a full white pattern, a full black pattern, and a circle white pattern at a first distance away from a light detector;
aligning a center of the circle white pattern and a center of a receiving lens of the light detector onto an alignment axis;
positioning the transparent display between the background and the light detector and at a position with a second distance away from the light detector;
displaying a circle transparent pattern on a center of the transparent display;
aligning a center of the circle transparent pattern onto the alignment axis;
measuring a full white luminance of the full white pattern, a full black luminance of the full black pattern and a circle white luminance of the circle white pattern represented on the background, through the transparent display, with the light detector; and calculating a purity of the transparent display using the following equation 1:

$$\text{Purity}(\%) = \frac{L_{CW} - L_{FK}}{L_{FW} - L_{FK}} \times 100 \quad \text{(Equation 1)}$$

wherein, $L_{FW}$ is the full white luminance, $L_{FK}$ is the full black luminance, and $L_{CW}$ is the circle white luminance.

10. The method according to claim 9, wherein the first distance is 1.5 m and the second distance is 0.5 m.

11. The method according to claim 9, wherein the circle white pattern includes a circle pattern having a first diameter and a full white level, and an ambient surrounding the circle pattern and having a full black level, and
wherein the first diameter corresponds to a 0.2° height based on a point 1.5 m away from the light detector.

12. The method according to claim 9, wherein the circle transparent pattern includes a circle pattern having a maximum white level of the transparent display and an ambient surrounding the circle pattern having a maximum black level of the transparent display, and
wherein a second diameter of the circle pattern corresponds to a 0.2° height based on a point 1.5 m away from the light detector and covers an area including at least 500 pixels of the transparent display.

13. The method according to claim 9, wherein a shape and a size of the circle white pattern and a receiving lens of the light detector are the same, and
a center of the circle white pattern, a center of the circle transparent pattern, and a center of the receiving lens are aligned in a straight line.

14. The method according to claim 9, wherein the background is further configured to represent a circle black pattern, and
wherein the method further comprises:
measuring a circle black luminance of the circle black pattern passing through the circle transparent pattern displayed on the transparent display;
calculating a criteria of the purity using the circle black luminance of the circle black pattern measured by the light detector; and
evaluating an allowance error in which the calculated purity is decided as the purity of the transparent display when a criteria is satisfied; and
repeating the aligning of the alignment axis when the criteria is not satisfied,
wherein the criteria is calculated by the following equation:

$$\text{Criteria} = \frac{|L_{FW} - L_{CW}| - |L_{FK} - L_{CK}|}{|L_{FW} - L_{CW}|} \times 100 \le 2(\%)$$

wherein $L_{FW}$ is the full white luminance, $L_{FK}$ is the full black luminance, $L_{CW}$ is the circle white luminance, and $L_{CK}$ is the circle black luminance.

15. The method according to claim 14, wherein the circle black pattern includes a circle pattern with a full black level having a first diameter and an ambient with a full white level, and
wherein the first diameter corresponds to a 0.2° height based on a point 1.5 m away from the light detector.

16. The method according to claim 9, wherein between the positioning of the background and the positioning of the transparent display, the method further comprises measuring a reference full white luminance of the full white pattern, a reference full black luminance of the full black pattern and a reference circle white luminance of the circle white pattern, by the light detector without the transparent display being positioned between the light detector and the background; and calculating a reference purity of the background by the following equation 2:

$$P_{ref} = \frac{L_{CW,w/o} - L_{FK,w/o}}{L_{FW,w/o} - L_{FK,w/o}} \quad \text{(Equation 2)}$$

wherein $L_{FW,w/o}$ is the reference full white luminance, $L_{FK,w/o}$ is the reference full black luminance, and $L_{CW,w/o}$ is the reference circle white luminance, wherein the purity calculated by the equation 1 is decided as a measured purity, and wherein a new purity of the transparent display is calculated by the following equation 3:

$$\text{Purity}(\%) = \frac{P_{exp}}{P_{ref}} \times 100 \quad \text{(Equation 3)}$$

wherein $P_{exp}$ is the measured purity, and $P_{ref}$ is the reference purity.

* * * * *